(12) United States Patent
Segman et al.

(10) Patent No.: US 11,819,317 B2
(45) Date of Patent: Nov. 21, 2023

(54) APPARATUS AND METHOD FOR USING ECG TO RECOVER PULSE WAVEFORM AND OTHER HEMODYNAMICS

(71) Applicant: CNOGA MEDICAL LTD., Caesarea (IL)

(72) Inventors: Yosef Segman, Caesarea (IL); Yehonatan Segman, Caesarea (IL)

(73) Assignee: CNOGA MEDICAL LTD., Caesarea (IL)

( * ) Notice: Subject to any disclaimer, the term of this patent is extended or adjusted under 35 U.S.C. 154(b) by 9 days.

(21) Appl. No.: 16/207,136

(22) Filed: Dec. 2, 2018

(65) Prior Publication Data

US 2020/0170518 A1 Jun. 4, 2020

(51) Int. Cl.
*A61B 5/00* (2006.01)
*A61B 5/0245* (2006.01)
*A61B 5/316* (2021.01)
*A61B 5/349* (2021.01)

(52) U.S. Cl.
CPC ............ *A61B 5/0245* (2013.01); *A61B 5/316* (2021.01); *A61B 5/349* (2021.01); *A61B 5/7235* (2013.01); *A61B 5/0006* (2013.01)

(58) Field of Classification Search
CPC .... A61N 1/3925; A61N 1/046; A61N 1/3975; A61N 1/3904; A61N 1/3968; A61N 1/3906; A61N 1/3912
See application file for complete search history.

(56) References Cited

U.S. PATENT DOCUMENTS

2010/0280396 A1 11/2010 Zhang
2013/0218038 A1 8/2013 Zhang

OTHER PUBLICATIONS

Luu Loc et al: "Using Moving Average Method to Recognize Systole and Diastole on Seismocardiogram without ECG Signal", 2018 40th Annual International Conference of the IEFE Engineering in Medicine and Biology Society (EMBC), IEFE, Jul. 18, 2018.
Ying-Wen Bai et al: "The combination of Kaiser window and moving average for the low-pass filtering of the remote ECG signals", Computer-Based Medical Systems, 2004. CBMS 2004. Proceedings. 17th IEE E Symposium on Bethesda, MD, USA, IEEE, Jun. 24, 2004.

*Primary Examiner* — Rex R Holmes
(74) *Attorney, Agent, or Firm* — Mark M. Friedman

(57) ABSTRACT

An apparatus generates a pulse (or other hemodynamic) signal from an ECG signal, and displays a waveform of that signal. An ECG unit comprises electrode(s) for receiving an ECG signal waveform from live tissue and for generating a digital ECG signal; a memory storage; hardware processor(s) configured to constantly apply an integral function to the digital ECG signal and display a waveform of the integral function during a time period. The waveform of the integral function has a shape of a pulse signal waveform of the subject during the time period. The integral function comprises $$PWF(t)_T = A\int_t^{t+T} F(ECG(u))du$$

ECG(u) represents an ECG over a specific time period using a specific time resolution. T is determined from the ECG(u) time resolution and pulse frequency, T satisfies the Nyquist sampling theory, t, u are time variables and A is a positive constant. The memory stores the integral function waveform. A weight function $$PWF(t)_T = A\int_t^{t+T} F(ECG(u)) \cdot W(u-t)du$$

may be included.

8 Claims, 10 Drawing Sheets

CARDIAC OUTPUT WAVEFORM

Cardiac Output = A • Stroke Volume • Pulse

Wherein A is a real positive constant and pulse is the number of beats in 60 seconds.

APPARATUS AND METHOD FOR USING ECG TO RECOVER PULSE WAVEFORM AND OTHER HEMODYNAMICS

FIELD AND BACKGROUND OF THE INVENTION

The invention is in the field of medical diagnostic devices and methods. More particularly, the invention aims to use an ECG to obtain a pulse waveform and other hemodynamic parameters.

An electrocardiograph, commonly called an ECG, is a graphic recording of the electrical impulses associated with the heart beat of a subject. It provides very useful diagnostic information.

SUMMARY OF THE INVENTION

One aspect of the invention is a medical apparatus configured to generate from an ECG signal, a signal corresponding to a pulse waveform of a mammalian subject, and to display a waveform of that signal, the apparatus comprising an ECG unit comprising at least one electrode, the ECG unit configured to obtain and output an ECG signal from live tissue of a mammalian subject and configured to generate a digital ECG signal during a period of time if a waveform of the ECG signal is not already digital; a memory storage for receiving and storing a waveform of the digital ECG signal during the period of time; one or more hardware processors configured to constantly apply an integral function to the digital ECG signal and initiate a display signal to a digital display device to display a waveform of the integral function during the period of time, wherein the waveform of the integral function has a shape of a pulse signal waveform of the subject taken during the period of time, wherein the integral function comprises:

$$PWF(t)_T = A\int_t^{t+T} F(ECG(u))du$$

wherein $PWF(t)_T$ is the recovered pulse waveform from the ECG signal and wherein $ECG(u)$ represents an ECG over a specific time period using a specific time resolution defined by a number of sampling points per unit time, where F is a pre-processing operator on ECG to reduce or eliminate noise before integration or to smooth or sharpen the digital ECG signal before integration, wherein T is determined from the $ECG(u)$ time resolution and from a pulse or ECG peak rate in which T satisfies the Nyquist sampling theory, wherein t, u are each time variables and wherein A is a positive constant, wherein the memory storage is configured to constantly store the waveform of the integral function having the shape of the pulse signal waveform, the one or more hardware processors configured to send instructions to display or print the waveform of the integral function having the shape of the pulse signal waveform.

In some embodiments, the integral function comprises $$PWF(t)_T = A\int_t^{t+T} F(ECG(u)) \cdot W(u-t)du$$

wherein $W(u)$ is a weight function.

In some embodiments, one or more of the ECG unit, memory storage, one or more hardware processors and digital display device are situated remotely from at least one other of the ECG unit, memory storage, one or more processors and digital display device.

In some embodiments, the one or more hardware processors are configured to obtain from the pulse signal waveform at least one of the following hemodynamic parameters of the subject during the period of time: (i) a hemodynamic blood pressure parameter that is at least one of (a) systolic blood pressure, (b) diastolic blood pressure, (ii) stroke volume, (iii) cardiac output, (iv) blood velocity, (v) blood viscosity, (vi) presence of congestive heart failure, (vii) presence of heart failure, (viii) peripheral blood perfusion, (ix) the location of the systolic blood pressure and the location of the diastolic blood pressure on the recovered pulse signal waveform, (x) resistance of the blood vessels, (xi) blood vessel stiffness, (xii) cardiac index and (xiii) a variation of any of the parameters "(i)" through "(xii)" obtained by applying a function to any of the parameters "(i)" through "(xii)". In some embodiments, the one or more hardware processors are configured to obtain from the pulse signal waveform at least one of the following hemodynamic parameters of the subject during the period of time: (i) systolic blood pressure (ii) diastolic blood pressure, and (iii) stroke volume. In some embodiments, the one or more hardware processors are configured to obtain resistance of the blood vessels of the subject during the period of time from the pulse signal waveform.

Another aspect of the invention is a method of generating from an ECG signal, a signal corresponding to a pulse waveform of a mammalian subject, and to display a waveform of that signal, the method comprising utilizing an ECG unit comprising at least one electrode to obtain and output an ECG signal from live tissue of a mammalian subject and to generate a digital ECG signal during a period of time if a waveform of the ECG signal is not already digital; storing a waveform of the digital ECG signal in a computer-readable memory storage; utilizing one or more hardware processors to constantly apply an integral function to the digital ECG signal and initiate a display signal to a digital display device to display a waveform of the integral function during the period of time, wherein the waveform of the integral function has a shape of a pulse signal waveform of the subject taken during the period of time, wherein the integral function comprises:

$$PWF(t)_T = A\int_t^{t+T} F(ECG(u))du$$

wherein $PWF(t)_T$ is the recovered pulse waveform from the ECG signal and wherein $ECG(u)$ represents an ECG over a specific time period using a specific time resolution defined by a number of sampling points per unit time, where F is a pre-processing operator on ECG to reduce or eliminate noise before integration or to smooth or sharpen the digital ECG signal before integration, wherein T is determined from the $ECG(u)$ time resolution and from a pulse or ECG peak rate in which T satisfies the Nyquist sampling theory, wherein t, u are each time variables and wherein A is a positive constant, wherein the memory storage constantly stores the waveform of the integral function having the shape of the pulse signal waveform; and initiating a display signal to a digital display device to constantly display the waveform of the integral function having the shape of the pulse signal waveform of the subject.

In some embodiments, the integral function comprises $$PWF(t)_T = A\int_t^{t+T} F(ECG(u)) \cdot W(u-t)du$$

wherein $W(u)$ is a weight function.

In some embodiments, one or more of the ECG unit, memory storage, one or more hardware processors and digital display device are situated remotely from at least one other of the ECG unit, memory storage, one or more processors and digital display device.

In some embodiments, the one or more hardware processors are configured to obtain from the pulse signal waveform at least one of the following hemodynamic parameters of the subject during the period of time: (i) a hemodynamic blood pressure parameter that is at least one of (a) systolic blood pressure, (b) diastolic blood pressure, (ii) stroke volume, (iii) cardiac output, (iv) blood velocity, (v) blood viscosity, (vi) presence of congestive heart failure, (vii) presence of heart failure, (viii) peripheral blood perfusion, (ix) the location of systolic blood pressure and the location of diastolic blood pressure on the recovered pulse signal waveform, (x) resistance of the blood vessels, (xi) blood vessel stiffness, (xii) cardiac index and (xiii) a variation of any of the parameters "(i)" through "(xii)" obtained by applying a function to any of the parameters "(i)" through "(xii)". In one or more embodiments, the one or more hardware processors are configured to obtain from the pulse signal waveform at least one of the following hemodynamic parameters of the subject: (i) systolic blood pressure (ii) diastolic blood pressure, and (iii) stroke volume during the period of time. In one or more embodiments, the one or more hardware processors are configured to obtain resistance of the blood vessels of the subject during the period of time from the pulse signal waveform.

A still further aspect of the invention is a non-transitory computer-readable storage medium having stored thereon an application executable by one or more hardware processors, the execution performing: using an ECG signal that was obtained from live tissue of a mammalian subject to generate a digital ECG signal during a period of time if a waveform of the ECG signal is not already digital; storing a waveform of the digital ECG signal in a computer-readable memory storage; utilizing the one or more hardware processors to constantly apply an integral function to the digital ECG signal and initiate a display signal to a digital display device to display a waveform of the integral function during the period of time, wherein the waveform of the integral function has a shape of a pulse signal waveform of the subject taken during the period of time, wherein the integral function comprises:

$$PWF(t)_T = A\int_t^{t+T} F(RCG(u))du$$

wherein $PWF(t)_T$ is the recovered pulse waveform from the ECG signal and wherein ECG(u) represents an ECG over a specific time period using a specific time resolution defined by a number of sampling points per unit time, where F is a pre-processing operator on ECG to reduce or eliminate noise before integration or to smooth or sharpen the digital ECG signal before integration, wherein T is determined from the ECG(u) time resolution and from a pulse or ECG peak rate in which T satisfies the Nyquist sampling theory, wherein t, u are each time variables and wherein A is a positive constant; and constantly storing on the memory storage the waveform of the integral function having the shape of the pulse signal waveform, initiating a display signal to a digital display device to constantly display the waveform of the integral function having the shape of the pulse signal waveform of the subject.

In some embodiments, the integral function comprises $$PWF(t)_T = A\int_t^{t+T} F(ECG(u)) \cdot W(u-t)du$$

wherein W(u) is a weight function.

In some embodiments, the execution of the stored application performs utilizing the one or more hardware processors to obtain from the pulse signal waveform at least one of the following hemodynamic parameters of the subject during the period of time: (i) a hemodynamic blood pressure parameter that is at least one of (a) systolic blood pressure, (b) diastolic blood pressure, (ii) stroke volume, (iii) cardiac output, (iv) blood velocity, (v) blood viscosity, (vi) presence of congestive heart failure, (vii) presence of heart failure, (viii) peripheral blood perfusion, (ix) the location of systolic blood pressure and the location of diastolic blood pressure on the recovered pulse signal waveform, (x) resistance of the blood vessels, (xi) blood vessel stiffness, (xii) cardiac index and (xiii) a variation of any of the parameters "(i)" through "(xii)" obtained by applying a function to any of the parameters "(i)" through "(xii)". In some embodiments, the execution of the stored application performs utilizing the one or more hardware processors to obtain from the pulse signal waveform at least one of the following hemodynamic parameters of the subject during the period of time: (i) systolic blood pressure (ii) diastolic blood pressure, and (iii) stroke volume. In some embodiments, execution of the stored application performs utilizing the one or more hardware processors to obtain resistance of the blood vessels of the subject during the period of time from the pulse signal waveform.

These and other features, aspects and advantages of the invention will become better understood with reference to the following drawings, descriptions and claims.

BRIEF DESCRIPTION OF THE DRAWINGS

Various embodiments are herein described, by way of example only, with reference to the accompanying drawings, wherein.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Figure 2A:
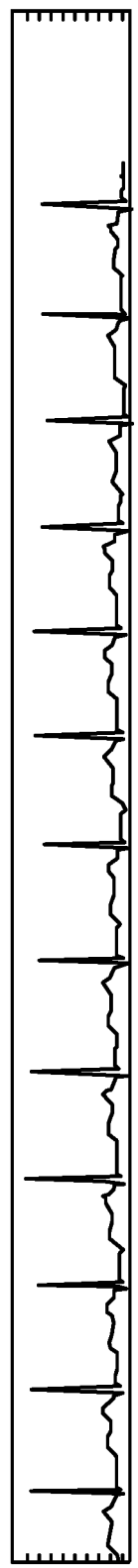
FIG. 2A is a graph of a patient's ECG downloaded from www.physionet.org.
Figure 2B:
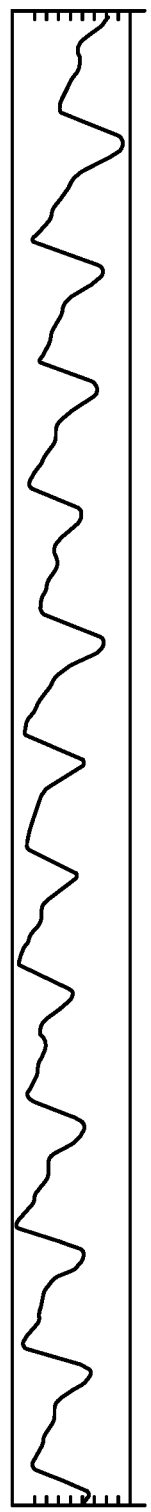
FIG. 2B is a graph of a pulse waveform derived from the ECG of FIG. 2A by applying a method and apparatus in accordance with an embodiment of the invention.
Figure 2C:
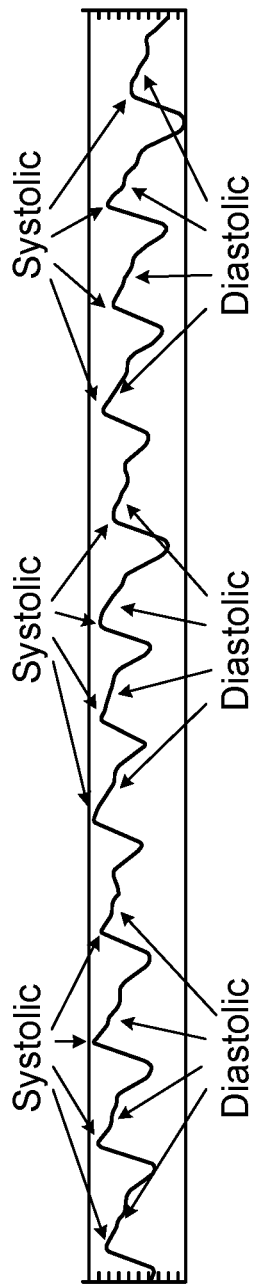
FIG. 2C is a graph of the pulse waveform of FIG. 2B designating locations indicating momentary systolic and diastolic blood pressure in accordance with an embodiment of the invention.
Figure 2D:
FIG. 2D is a graph of the pulse waveform of FIG. 2B showing stroke volume waveform in accordance with an embodiment of the invention.
Figure 2E:
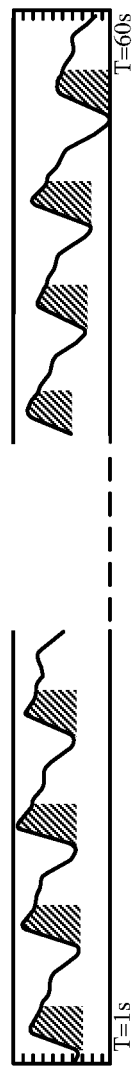
FIG. 2E is a graph of the pulse waveform of FIG. 2B showing cardiac output waveform in accordance with an embodiment of the invention.

The invention generally provides a medical apparatus and method configured to generate, from an ECG signal of a mammalian subject during a certain time period, a signal corresponding to a pulse waveform of a mammalian subject and to display a waveform of that signal. In some embodiments, the apparatus or method obtains a further signal from the pulse signal. In some embodiments (of each of the apparatus, method(s) and computer-readable medium) a pulse waveform is a blood pressure waveform if the systolic and diastolic values appear on the pulse signal waveform indicating the momentary blood pressure. In that regard, as shown in FIG. 2C, usually the pulse signal waveform's peaks represents the momentary systolic blood pressure values and a point along the slope of the waveform between the current peak and the next major minimum represents the momentary diastolic blood pressure. In other embodiments the pulse signal waveform is a stroke volume waveform if the stroke volume values appear on the pulse signal waveform indicating the blood volume per heart stroke, as seen in FIG. 2D and is a cardiac output waveform (see FIG. 2E) showing the total cardiac output per minute (stroke volume times pulse times a positive constant). The recovered signal from ECG is a signal representing hemodynamic physiological status of the mammalian subject during that time period, and displays a waveform of that further signal. The hemodynamic status is a set of bioparameters that includes at least one of (a) systolic blood pressure, (b) diastolic blood pressure, (ii) stroke volume, (iii) cardiac output, (iv) blood velocity, (v) blood viscosity, (vi) presence of congestive heart failure, (vii) presence of heart failure, (viii) peripheral blood perfusion, (ix) the location of systolic blood pressure and the location of diastolic blood pressure on the recovered pulse signal waveform, (x) resistance of the blood vessels, (xi) blood vessel stiffness, (xii) cardiac index and (xiii) a variation of any of the parameters "(i)" through "(xii)" obtained by applying a function to any of the parameters "(i)" through "(xii)".

In one example, the apparatus includes an ECG unit. The ECG unit comprises at least one electrode for obtaining and outputting an ECG signal from live tissue of a mammalian subject and for generating a digital ECG signal during a period of time if the ECG signal waveform is not already digital. The apparatus also has in some embodiments a memory storage for receiving and storing real time digital ECG data from the digital ECG signal during the period of time.

The apparatus 10 also has a processing unit which may include one or more hardware processors 40 configured to constantly apply an integral function to the digital ECG signal and initiate a display signal to a digital display device to display a waveform of the integral function during the period of time, wherein (in the case where the hemodynamic parameter is the pulse) the waveform of the integral function has a shape of a pulse signal waveform of the subject taken during the period of time, wherein the integral function comprises:

$$PWF(t)_T = A\int_t^{t+T} ECG(u)du$$

wherein $PWF(t)_T$ is the recovered pulse waveform from the ECG signal and wherein $ECG(u)$ represents an ECG over a specific time period using a specific time resolution defined by a number of sampling points per unit time such as a second or a minute or another time interval, wherein T (which is the length of the integral) is determined from the ECG(u) time resolution and from a pulse or ECG peak rate (frequency of the peaks in the ECG signal) in which T satisfies the Nyquist sampling theory, wherein t, u are each time variables and wherein A is a positive constant.

In some embodiments a mathematical F operation in the form $$PWF(t)_T = A\int_t^{t+T} F(ECG(u))du$$

is first performed on the ECG. The outcome of the F operation in one non-limiting example is a convolution operation resulting in smoothing the ECG by various low pass filter or alternatively the convolution operation results in sharpening the ECG by using a high pass filter or any other filter. Another example of the F operation is a noise reduction or noise elimination.

The memory storage stores the pulse waveform outcomes (i.e. the waveform of the integral function having the shape of the pulse signal waveform). The one or more hardware processors 40 may also be configured to send instructions to display or print the waveform of the integral function having the shape of the pulse signal waveform.

Optionally, the integral function comprises $$PWF(t)_T = A\int_t^{t+T} F(ECG(u)) \cdot W(u-t)du$$

wherein $PWF(t)_T$ is the recovered pulse waveform from the ECG signal and wherein $W(u)$ is a windows weight function, for example a smoothing weight function which may be Gaussian or non-Gaussian.

Non-limiting examples of a window function are:
$W(t)=1$ for any $-1 \le t \le 1$; otherwise $W(t)=0$.
$W(t)=k*\exp(-a*|t|)$ for any real number t, "a" is a positive real number where "||" means absolute value.
$W(t)=k*\exp(-a*t^2)$ for any real number t, "a" is a positive number. W in this case is a Gaussian weighting function. In the last two examples, k is a real constant.

Applicant discovered that the waveform of the integral function of the ECG has a shape of a pulse signal waveform of the subject that was taken during the period of time. A digital display device or printer device is configured to receive the display signal and display or print the waveform of the integral function having the shape of the hemodynamic signal waveform. The memory and one or more processors can be integrated into one physical device or they can be remote from the ECG unit. Anyone can obtain a waveform that has the shape of a pulse or other hemodynamic parameter from an ECG device without any other device or technical assistance. A doctor can see the patient's pulse from the display of the apparatus and from the output of the method.

Typically, to obtain hemodynamic parameters, including but not limited to pulse, would require a separate device. The invention generates a display or printout of these hemodynamic parameters in some embodiments from the same ECG unit that produces the ECG signal.

The principles and operation of Apparatus and Method for Using ECG to Recover Pulse Waveform and Other Hemodynamics may be better understood with reference to the drawings and the accompanying description.

Figure 1:
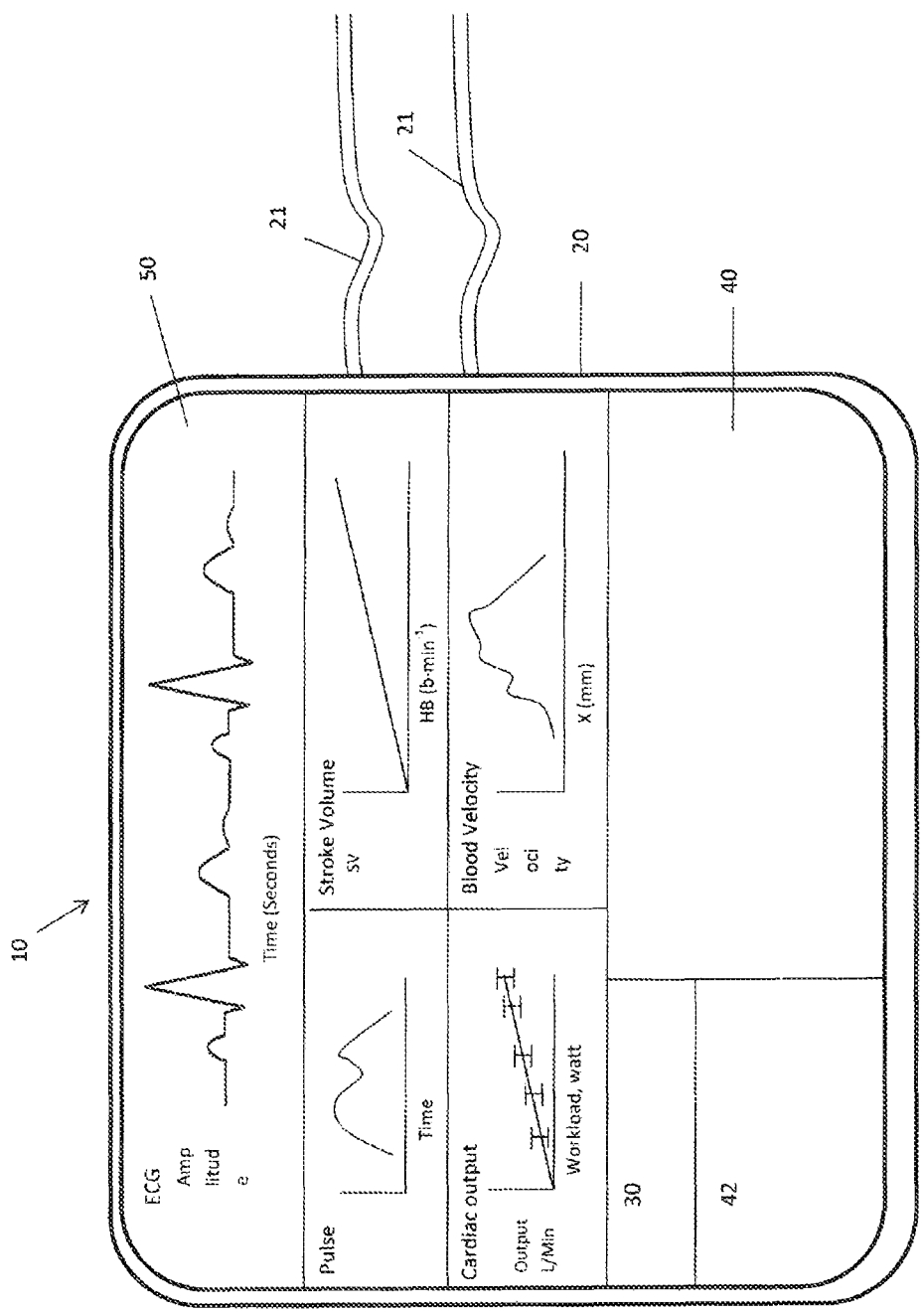
FIG. 1 is a schematic illustration of an ECG unit displaying an ECG and a pulse waveform and other hemodynamic parameters, in accordance with one embodiment of the invention.
Figure 3:
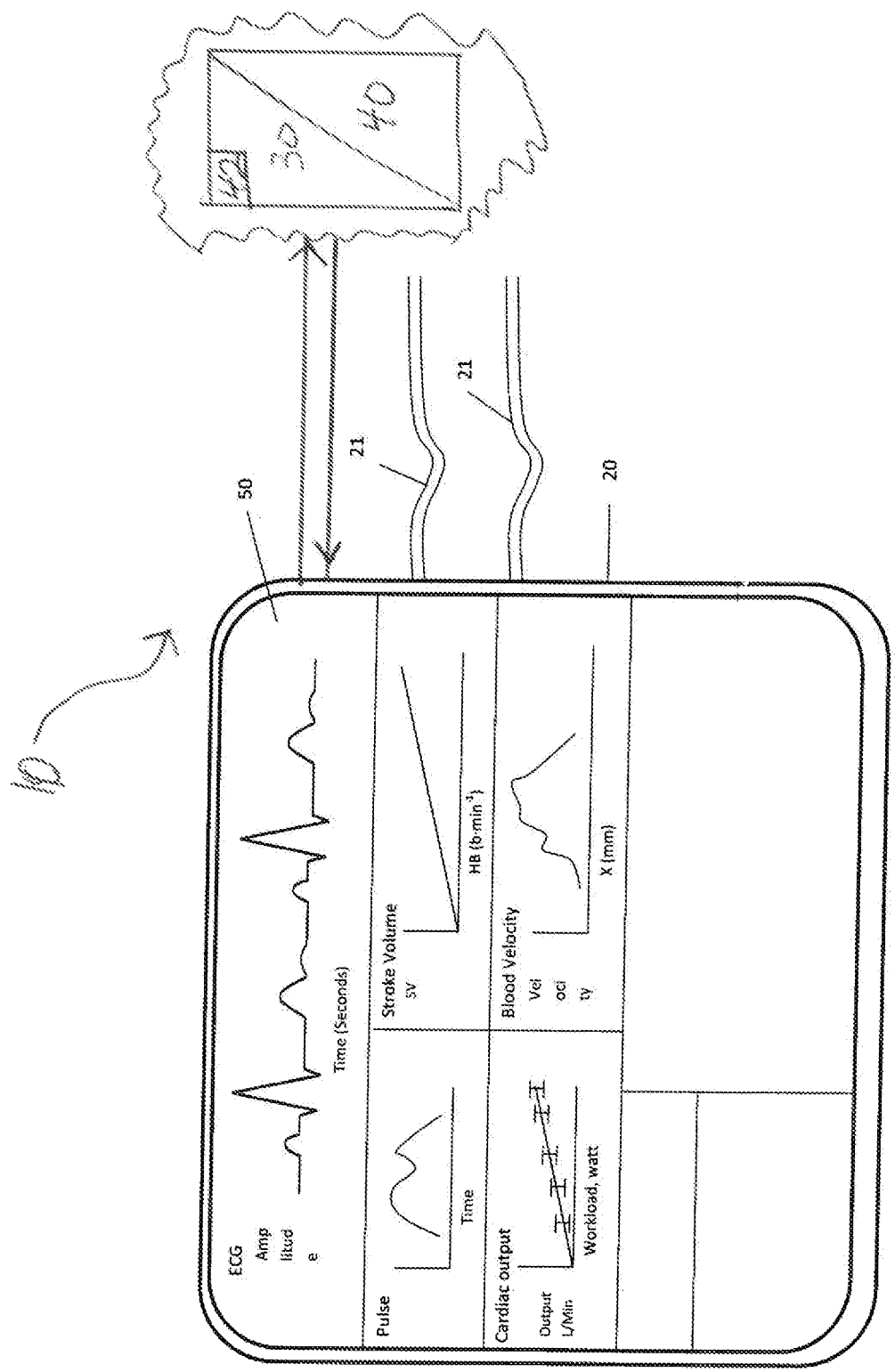
FIG. 3 is a schematic illustration of a system in which the memory storage and one or more processors are and remote from the ECG unit and display or printer device and accessible by telecommunications network, in accordance with one embodiment of the invention.

As seen from FIGS. 1-3, the invention, in one embodiment, is a medical apparatus 10 configured to generate, from an ECG signal, a signal corresponding to a pulse waveform of a mammalian subject, and to display a waveform of that signal. The apparatus 10 comprises an ECG unit 20 which may comprise at least one electrode 21 and is configured to obtain and output an ECG signal from live tissue of a mammalian subject during a time period. The ECG unit is configured to generate a digital ECG signal during the period of time if the waveform of the ECG signal is not already digital.

Apparatus 10 may comprise a memory storage 30 configured to receive and store (for example constantly or continuously store) the waveform of the digital ECG signal during the period of time. Apparatus 10 may also comprise one or more hardware processors 40 configured to constantly apply an integral function to the digital ECG signal and initiate a display signal(s) to a digital display device 50 to display (for example to constantly or continuously display) a waveform of the integral function during the period of time, wherein the waveform of the integral function has a shape of a pulse signal waveform of the subject taken during the period of time, wherein the integral function comprises:

$$PWF(t)_T = A\int_t^{t+T} F(ECG(u))du$$

wherein $PWF(t)_T$ is the recovered pulse waveform from the ECG signal and wherein ECG(u) represents an ECG over a specific time period using a specific time resolution defined by a number of sampling points per unit time such as a second, minute or other time interval, where F is a pre-processing operator on ECG to reduce or eliminate noise before integration or to smooth or sharpen the digital ECG signal before integration, wherein T (which is the length of the integral) is determined from the ECG(u) time resolution and from a pulse or ECG peak rate in which T satisfies the Nyquist sampling theory, wherein t, u are each time variables and wherein A is a positive constant. Common non-limiting examples of a time interval are seconds or minutes.

In any embodiment herein, the time resolution means the number of sampling point per time interval (the most common time interval being a second). For example, a resolution of 250 hz means 250 sampling points for each second. Although computing T according to Nyquist sampling theory for 250 hz is well known in some embodiments one should also consider the number of beats within T. For example, if T does not contain any beats in some embodiments one would increase T so that each time one performs integration over T at least one beat is incorporated. In some cases, therefore, we may need more than a single beat.

The number of beats per minute can be determined from the frequency of the peaks in the ECG signal. For example, if the ECG unit 20 records the ECG of the mammalian subject for 10 seconds, and if the one or more hardware processors 40 counts and determines that there are 12 peaks during the 10 seconds, then the one or more hardware processors 40 may determine that there are 1.2 beats per second or that there are 72 beats per minute. This is commonly call "pulse rate".

"Pulse" means the number of beats per time interval. In some embodiments, the invention utilizes either the pulse or the number of peaks in the ECG signal per time interval to help determine T. Accordingly, in this patent application the phrase "from a pulse or ECG peak rate" means from the pulse of the mammalian subject or from the number of peaks in the ECG signal of the mammalian subject per time interval.

The memory storage 30 may store the pulse waveform outcome, which is the waveform of the integral function having a shape of the pulse signal waveform. The one or more hardware processors 40 may be configured to send an instruction to display or print the waveform of the integral function having the shape of the pulse signal waveform.

Optionally, the integral function comprises $$PWF(t)_T = A\int_t^{t+T} F(ECG(u)) \cdot W(u-t)du$$

wherein $PWF(t)_T$ is the recovered pulse waveform from the ECG signal and wherein ECG(u) represents an ECG over a specific time period using a specific time resolution defined by a number of sampling points per unit time such as a second, minute or other time interval, where F is a pre-processing operator on ECG to reduce or eliminate noise before integration or to smooth or sharpen the digital ECG signal before integration, wherein T (which is the length of the integral) is determined from the ECG(u) time resolution and from a pulse or ECG peak rate in which T satisfies the Nyquist sampling theory, wherein t, u are each time variables and wherein A is a positive constant, and wherein W(u) is a weight function, for example a smoothing weight function, for example a Gaussian window function providing focal points on the location of t.

Non-limiting examples of a window function are:
W(t)=1 for any −1≤t≤1; otherwise W(t)=0.
W(t)=k*exp(−a*|t|) for any real number t, "a" is a positive real number where "||" means absolute value.
W(t)=k*exp(−a*t^2) for any real number t, "a" is a positive number. W in this case is a Gaussian weighting function. In the last two examples, k is a real constant.

Optionally, as seen in FIG. 3, the one or more of the ECG unit, memory storage, one or more hardware processors and digital display device are situated remotely from at least one other of the pulse unit, memory storage, one or more processors and digital display device. In that case apparatus 10 would be described as a system.

Pulse is not the only hemodynamic parameter obtainable from the ECG signal using the invention. In some embodiments, the one or more hardware processors 40 are configured to obtain (for example constantly obtain) from the pulse signal waveform at least one of the following hemodynamic parameters of the subject (e.g. during the period of time): (i) a hemodynamic blood pressure parameter that is at least one of (a) systolic blood pressure, (b) diastolic blood pressure, (ii) stroke volume, (iii) cardiac output, (iv) blood velocity, (v) blood viscosity, (vi) presence of congestive heart failure, (vii) presence of heart failure, (viii) resistance of the blood vessels, (ix) the location of systolic blood pressure and the location of diastolic blood pressure on the recovered pulse waveform, (x) peripheral blood perfusion, (xi) blood vessel stiffness, (xii) cardiac index and (xiii) a variation of any of the parameters "(i)" through "(xii)" obtained by applying hemodynamic algorithm(s) to any of the parameters "(i)" through "(xii)".

In some embodiments, the one or more hardware processors 40 are configured to obtain (for example constantly obtain) from the pulse signal waveform at least one of the following hemodynamic parameters of the subject (e.g. during the period of time): (i) systolic blood pressure (ii) diastolic blood pressure, and (iii) stroke volume. In some embodiments, the one or more hardware processors 40 are configured to obtain resistance of the blood vessels of the subject (e.g. during the period of time) from the pulse signal waveform.

A memory storage component of a computer system, such as a memory storage 30 of a computer system, is configured to receive and store the waveform of the digital ECG signal (for example in real time) during the period of time. In general, the computer system, in all embodiments, includes all necessary hardware 40 and software 42 to perform the functions described herein.

The apparatus 10 in some embodiments includes a digital display device 50 or printer device 50 configured to receive the display signal and display or print the waveform of the integral function having the shape of the pulse signal waveform (or other hemodynamic parameter of the subject). In some embodiments, the digital display device 50 is a digital display screen or is otherwise integrated with the ECG unit 20, memory storage 30 and/or hardware processor(s) 40 as a single device. In other embodiments, the digital display device 50 is separate.

An example of the application of an embodiment of the invention is as follows. FIG. 2A shows a graph of a live human patient's ECG downloaded from www.physionet.org. FIG. 2B is a graph of a pulse waveform derived from the ECG of FIG. 2A by applying a method and apparatus in accordance with an embodiment of the invention. In order to yield the pulse signal waveform of FIG. 2B, Applicant downloaded the ECG from physionet.org which was already in digital form and sampled the ECG waveform at 360 hz, namely 360 sampling points per second. Other sampling rates consistent with Nyquist sampling theory could have been used consistent with the invention provided they were consistent with Nyquist sampling theory. Applicant utilized the ECG unit, memory storage 30 and one or more processors 40 as described in apparatus 10 and method 100. For example memory storage 30 was used so that one or more hardware processors 40 could compute the T interval according to the Nyquist sampling theory since T is determined from the ECG(u) time resolution and from a pulse or ECG peak rate in which T satisfies the Nyquist sampling theory. As a result of using apparatus 10 or method 100, Applicant obtained the pulse waveform displayed in FIG. 2B after applying the integral function on the ECG waveform of FIG. 2A.

Figure 4:
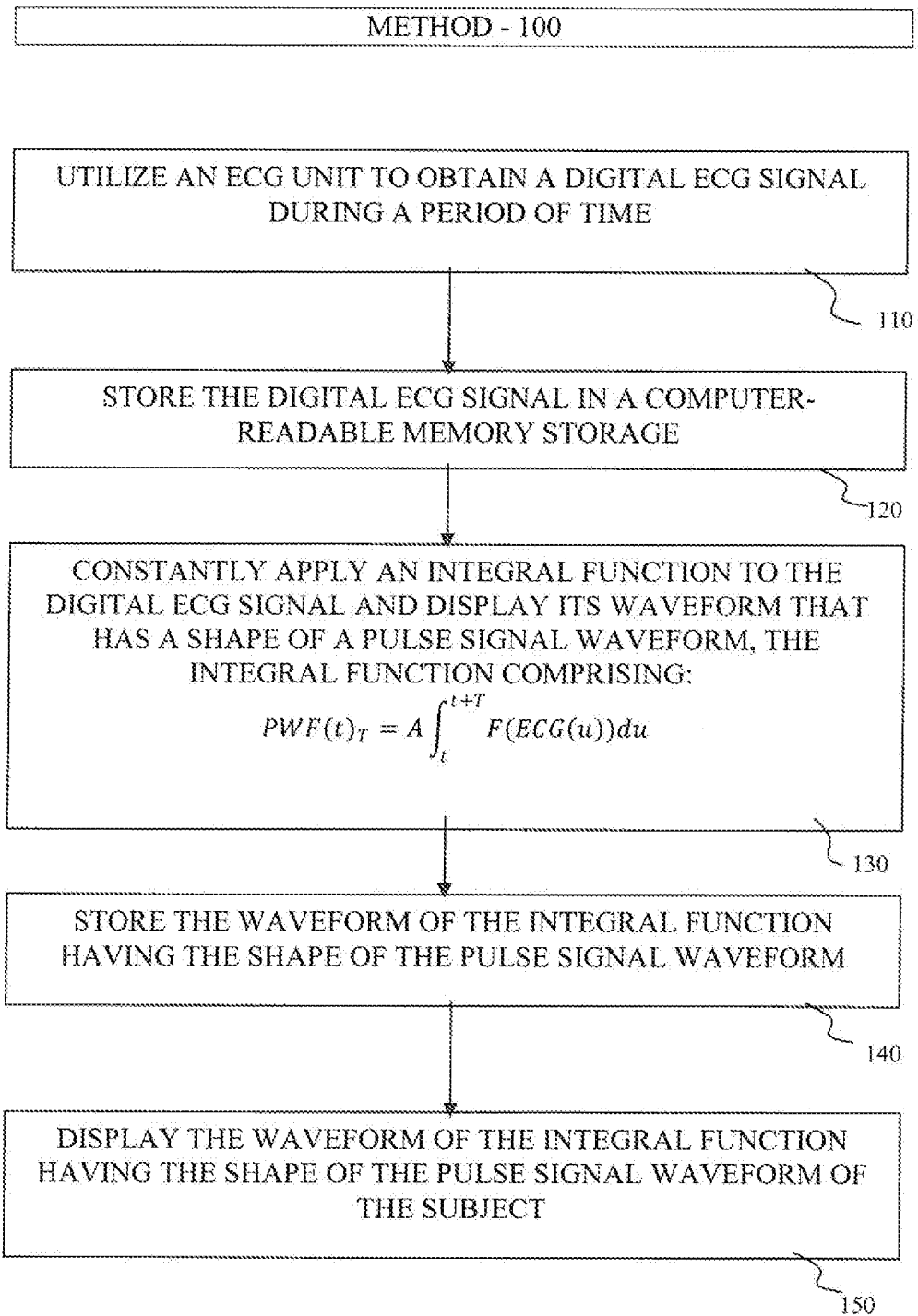
FIG. 4 is a flowchart showing a method of the invention.

As seen in FIG. 4, a further embodiment of the invention is a method 100 of generating from an ECG signal, a signal corresponding to a pulse waveform of a mammalian subject, and to display a waveform of that signal. In some embodiments, method 100 comprises a step 110 of utilizing an ECG unit 20 comprising at least one electrode to obtain and output an ECG signal from live tissue of a mammalian subject and to generate a digital ECG signal during a period of time if the waveform of the ECG signal is not already digital.

Method 100 may also comprise a step 120 of storing the waveform of the digital ECG signal in a computer-readable memory storage.

Method 100 in some embodiments includes a step 130 of utilizing one or more hardware processors 40 to constantly apply an integral function to the digital ECG signal and in some embodiments also initiate a display signal(s) to a digital display device to display (for example constantly or continuously) a waveform of the integral function during the period of time. In some embodiments of method 100, the digital display device 50 is simply a digital display screen or is otherwise integrated with the ECG unit 20, memory storage 30 and/or hardware processor(s) 40 as a single device. In other embodiments, the digital display device 50 is separate.

The waveform of the integral function has a shape of a pulse signal waveform of the subject taken during the period of time, wherein the integral function comprises:

$$PWF(t)_T = A\int_t^{t+T} F(ECG(u)) du$$

wherein $PWF(t)_T$ is the recovered pulse waveform from the ECG signal and wherein ECG(u) represents an ECG over a specific time period using a specific time resolution defined by a number of sampling points per unit time such as a second, minute or other time interval, where F is a pre-processing operator on ECG to reduce or eliminate noise before integration or to smooth or sharpen the digital ECG signal before integration, wherein T (which is the length of the integral) is determined from the ECG(u) time resolution and from a pulse or ECG peak rate in which T satisfies the Nyquist sampling theory, wherein t, u are each time variables and wherein A is a positive constant.

Method 100 in some embodiments includes a step of 140 of having the memory storage store (for example constantly store) the waveform of the integral function that has a shape of the pulse signal waveform.

Method 100 may include a step 150 of initiating a display signal(s) to a digital display device to display (for example constantly display) the waveform of the integral function having the shape of the pulse signal waveform of the subject.

Figure 5:
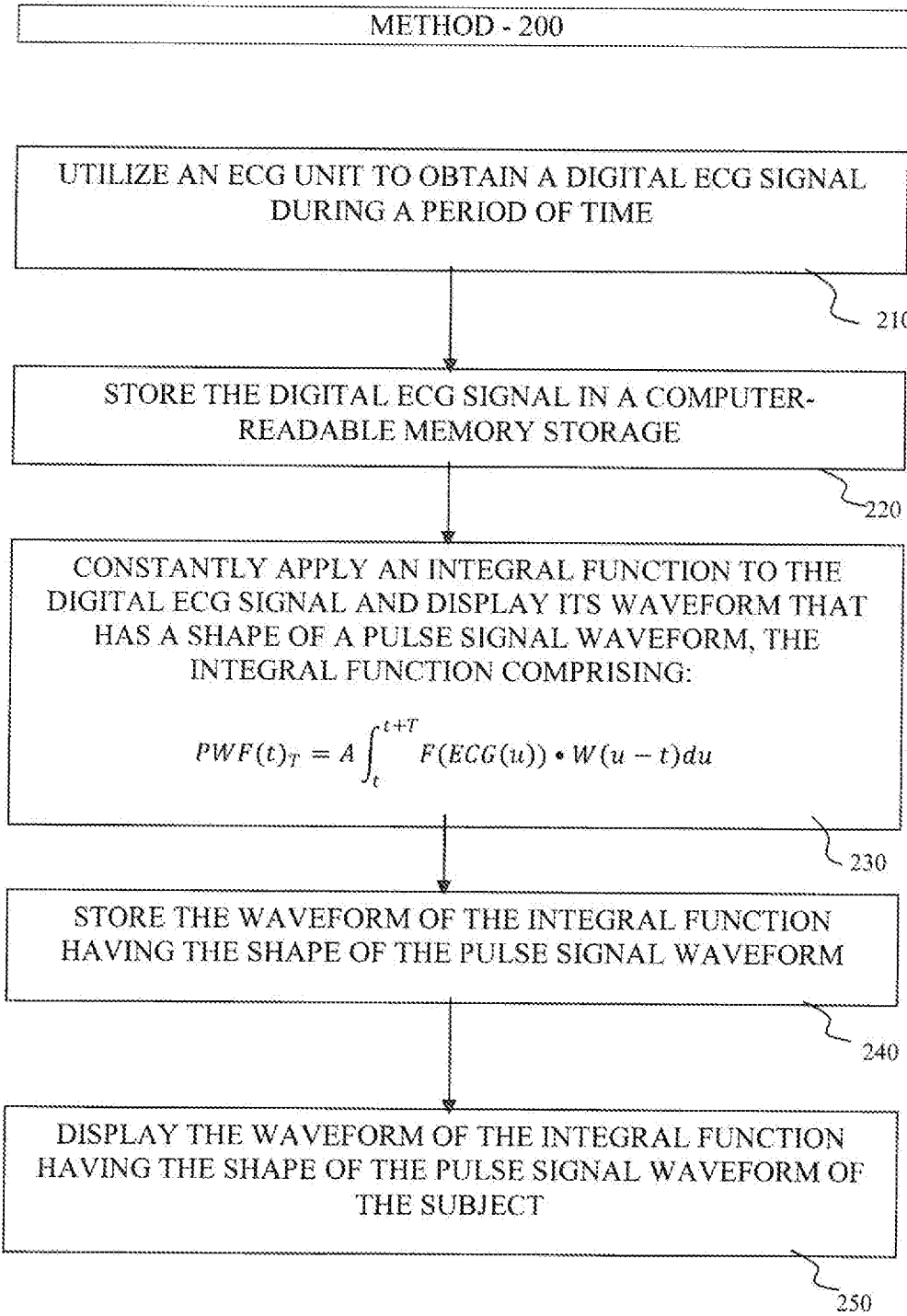
FIG. 5 is a flowchart showing a further method of the invention.

Optionally, as seen in FIG. 5, a weight function such as a smoothing weight function is included in the integral function. For example, in some embodiments, the integral function comprises $$PWF(t)_T = A\int_t^{t+T} F(ECG(u)) \cdot W(u-t) du$$

wherein $PWF(t)_T$ is the recovered pulse waveform from the ECG signal and wherein ECG(u) represents an ECG over a specific time period using a specific time resolution defined by a number of sampling points per unit time, where F is a pre-processing operator on ECG to reduce or eliminate noise before integration or to smooth or sharpen the digital ECG signal before integration, wherein T (which is the length of the integral) is determined from the ECG(u) time resolution and from a pulse or ECG peak rate in which T satisfies the Nyquist sampling theory, wherein t, u are each time variables and wherein A is a positive constant and wherein W(u) is a weight function such as a smoothing weight function, for example a Gaussian weight function (which may be a Gaussian window function) providing focal points on the location of t.

Non-limiting examples of a window function are:
W(t)=1 for any −1≤t≤1; otherwise (W(t)=0.
W(t)=k*exp(−a*|t|) for any real number t, "a" is a positive real number where "||" means absolute value.
W(t)=k*exp(−a*t^2) for any real number t, "a" is a positive number. W in this case is a Gaussian weighting function. In the last two examples, k is a real constant.

FIG. 5 shows a flow chart for a method 200 having steps 210, 220, 230, 240 and 250 similar to the steps 110, 120, 130, 140, 150 of method 100 except that step 230 utilizes the integral function having the weight function $$PWF(t)_T = A\int_t^{t+T} F(ECG(u)) \cdot W(u-t) du$$

Optionally, as with apparatus 10, one or more of the ECG unit 20, memory storage 30, one or more hardware processors 40 and digital display device 50 are situated remotely from at least one other of the ECG unit, memory storage, one or more hardware processors 40 and digital display device 50.

As with apparatus 10, in method 100, the one or more hardware processors 40 are configured to obtain (for example constantly) from the pulse signal waveform at least one of the following hemodynamic parameters of the subject (e.g. during the period of time): (i) a hemodynamic blood pressure parameter that is at least one of (a) systolic blood pressure, (b) diastolic blood pressure, (ii) stroke volume, (iii) cardiac output, (iv) blood velocity, (v) blood viscosity, (vi) presence of congestive heart failure, (vii) presence of heart failure, (viii) peripheral blood perfusion, (ix) the location of systolic blood pressure and the location of diastolic blood pressure on the recovered pulse signal waveform, (x) resistance of the blood vessels, (xi) blood vessel stiffness, (xii) cardiac index and (xiii) a variation of any of the parameters "(i)" through "(xii)" obtained by applying a function to any of the parameters "(i)" through "(xii)". In some embodiments, the one or more hardware processors are configured to obtain from the pulse signal waveform at least one of the following hemodynamic parameters of the subject (e.g. during the period of time): (i) systolic blood pressure (ii) diastolic blood pressure, and (iii) stroke volume. In some embodiments, the one or more hardware processors 40 are configured to obtain (for example constantly) resistance of the blood vessels of the subject (e.g. during the period of time) from the pulse signal waveform.

In general, the components used in the methods 100, 200 of the invention are the same as in the apparatus 10 of the invention. Accordingly, the variations in the embodiments of apparatus 10 may be used to vary the embodiments of method 100 or method 200.

Figure 6:
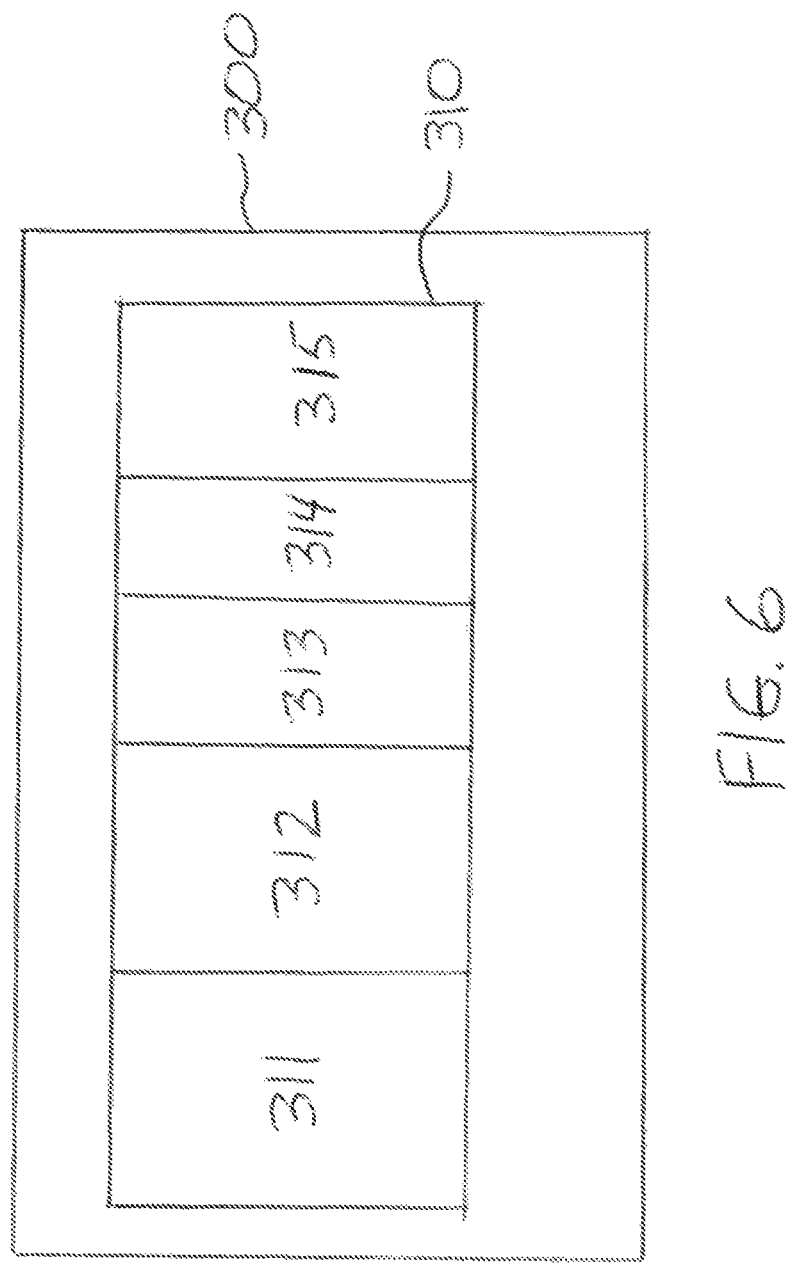
FIG. 6 is a schematic illustration of modules of an application stored on a non-transitory computer-readable medium and executed by one or more processors in accordance with an embodiment of the invention.

As seen from FIG. 6, a further embodiment of the invention is a non-transitory computer-readable storage medium 300 having stored thereon an application 310 (for example software) executable by one or more hardware processors, the execution of the application (for example software) performing the following steps:

using an ECG signal that was obtained from live tissue of a mammalian subject to generate a digital ECG signal during a period of time if the ECG signal waveform is not already digital, storing the digital ECG signal waveform in a computer-readable memory storage, utilizing the one or more hardware processors to constantly apply an integral function to the digital ECG signal and initiate a display signal to a digital display device to display a waveform of the integral function during the period of time, wherein the waveform of the integral function has a shape of a pulse signal waveform of the subject taken during the period of time, wherein the integral function comprises:

$$PWF(t)_T = A\int_t^{t+T} F(ECG(u))du$$

wherein $PWF(t)_T$ is the recovered pulse waveform from the ECG signal and wherein $ECG(u)$ represents an ECG over a specific time period using a specific time resolution defined by a number of sampling points per unit time, where F is a pre-processing operator on ECG to reduce or eliminate noise before integration or to smooth or sharpen the digital ECG signal before integration, wherein T (which is the length of the integral) is determined from the ECG(u) time resolution and from a pulse or ECG peak rate in which T satisfies the Nyquist sampling theory, wherein t, u are each time variables, wherein t, u are each time variables and wherein A is a positive constant; and storing (for example constantly) on the memory storage the waveform of the integral function having the shape of the pulse signal waveform. In some embodiments, a further executed step is initiating a display signal(s) to a digital display device to display (for example to constantly display) the waveform of the integral function having the shape of the pulse signal waveform of the subject.

Optionally, the integral function also includes a weight function such as in the following function:

$$PWF(t)_T = A\int_t^{t+T} F(ECG(u)) \cdot W(u-t)du$$

wherein $PWF(t)_T$ is the recovered pulse waveform from the ECG signal and wherein $ECG(u)$ represents an ECG over a specific time period using a specific time resolution defined by a number of sampling points per unit time such as a second, minute or other time interval, where F is a pre-processing operator on ECG to reduce or eliminate noise before integration or to smooth or sharpen the digital ECG signal before integration, wherein T (which is the length of the integral) is determined from the ECG(u) time resolution and from a pulse or ECG peak rate in which T satisfies the Nyquist sampling theory, wherein t, u are each time variables and wherein A is a positive constant and wherein W(u) is a weight function such as a smoothing weight function, for example a Gaussian weight function (which may be a Gaussian window function) providing focal points on the location of t.

Non-limiting examples of a window function are:
$W(t)=1$ for any $-1 \le t \le 1$; otherwise $W(t)=0$.
$W(t)=k*\exp(-a*|t|)$ for any real number t, "a" is a positive real number where "||" means absolute value.
$W(t)=k*\exp(-a*t^2)$ for any real number t, "a" is a positive number. W in this case is a Gaussian weighting function. In the last two examples, k is a real constant.

As with apparatus 10 and methods 100, 200, the non-transitory computer-readable storage medium 300 is configured to perform utilizing the one or more hardware processors to obtain (for example constantly) from the pulse signal waveform at least one of the following hemodynamic parameters of the subject (e.g. during the period of time): (i) a hemodynamic blood pressure parameter that is at least one of (a) systolic blood pressure, (b) diastolic blood pressure, (ii) stroke volume, (iii) cardiac output, (iv) blood velocity, (v) blood viscosity, (vi) presence of congestive heart failure, (vii) presence of heart failure, (viii) peripheral blood perfusion, (ix) the location of the systolic blood pressure and the location of the diastolic blood pressure on the recovered pulse signal waveform, (x) resistance of the blood vessels, (xi) blood vessel stiffness, (xii) cardiac index and (xiii) a variation of any of the parameters "(i)" through "(xii)" obtained by applying a function to any of the parameters "(i)" through "(xii)". In some embodiments, the one or more hardware processors are configured to obtain from the pulse signal waveform at least one of the following hemodynamic parameters of the subject (e.g. during the period of time): (i) systolic blood pressure (ii) diastolic blood pressure, and (iii) stroke volume. In some embodiments, the one or more hardware processors are configured to obtain (for example constantly) resistance of the blood vessels of the subject (e.g. during the period of time) from the pulse signal waveform.

In some embodiments of medium 300, as shown in FIG. 6, one or more of the above steps performed by executing the application 310 stored on medium 300 may be performed by executing different modules of application 310. For example, executing module 311 may perform using the ECG signal to generate the digital ECG signal, executing module 312 may perform storing the digital ECG signal waveform in the computer-readable memory storage, executing module 313 may perform utilizing the one or more hardware processors to constantly apply the integral function to the digital ECG signal and initiate a display signal to a digital display device to display a waveform of the integral function during the period of time, executing module 314 may perform storing on the memory storage the waveform of the integral function having the shape of the pulse signal waveform. In some embodiments, executing a module 315 may perform initiating a display signal to a digital display device to display the waveform of the integral function having the shape of the pulse signal waveform of the subject.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A medical apparatus configured to generate from an ECG signal, a signal corresponding to a pulse signal waveform of a mammalian subject, and to display a waveform of that signal, the apparatus comprising:
an ECG unit comprising at least one electrode, the ECG unit configured to obtain and output the ECG signal from live tissue of the mammalian subject and configured to generate a digital ECG signal during a period of time if the waveform of the ECG signal is not already digital;
a memory storage for receiving and storing the waveform of the digital ECG signal during the period of time;
one or more hardware processors configured to constantly apply an integral function to the digital ECG signal and initiate a display signal to a digital display device to display the waveform of the integral function during the period of time, wherein the waveform of the integral function has a shape of the pulse signal waveform of the subject taken during the period of time, wherein the integral function comprises:

$$PWF(t)_T = A\int_t^{t+T} F(ECG(u)) du$$

wherein $PWF(t)_T$ is the pulse signal waveform from the ECG signal and wherein $ECG(u)$ represents the digital ECG signal over a specific time period using a specific time resolution defined by a number of sampling points per unit time, where F is a pre-processing operator on the digital ECG signal to reduce or eliminate noise before integration or to smooth or sharpen the digital ECG signal before integration, wherein T is determined from the $ECG(u)$ time resolution and from a pulse or ECG peak rate in which T satisfies the Nyquist sampling theory, wherein t, u are each time variables and wherein A is a positive constant,
wherein the memory storage is configured to constantly store the waveform of the integral function having the shape of the pulse signal waveform,
the one or more hardware processors configured to send instructions to display or print the waveform of the integral function having the shape of the pulse signal waveform.

2. The apparatus of claim 1, wherein the integral function comprises $$PWF(t)_T = A\int_t^{t+T} F(ECG(u)) \cdot W(u-t) du$$

wherein $W(u-t)$ is a weight function.

3. The apparatus of claim 1, wherein one or more of the ECG unit, memory storage, one or more hardware processors and digital display device are situated remotely from at least one other of the ECG unit, memory storage, one or more processors and digital display device.

4. A method of generating from an ECG signal, a signal corresponding to a pulse signal waveform of a mammalian subject, and to display a waveform of that signal, the method comprising:
utilizing an ECG unit comprising at least one electrode to obtain and output the ECG signal from live tissue of the mammalian subject and to generate a digital ECG signal during a period of time if the waveform of the ECG signal is not already digital;
storing the waveform of the digital ECG signal in a computer-readable memory storage;
utilizing one or more hardware processors to constantly apply an integral function to the digital ECG signal and initiate a display signal to a digital display device to display the waveform of the integral function during the period of time, wherein the waveform of the integral function has a shape of the pulse signal waveform of the subject taken during the period of time, wherein the integral function comprises:

$$PWF(t)_T = A\int_t^{t+T} F(ECG(u)) du$$

wherein $PWF(t)_T$ is the pulse signal waveform from the digital ECG signal and wherein $ECG(u)$ represents the digital ECG signal over a specific time period using a specific time resolution defined by a number of sampling points per unit time, where F is a pre-processing operator on ECG to reduce or eliminate noise before integration or to smooth or sharpen the digital ECG signal before integration, wherein T is determined from the $ECG(u)$ time resolution and from a pulse or ECG peak rate in which T satisfies the Nyquist sampling theory, wherein t, u are each time variables and wherein A is a positive constant,
wherein the memory storage constantly stores the waveform of the integral function having the shape of the pulse signal waveform; and
initiating a display signal to a digital display device to constantly display the waveform of the integral function having the shape of the pulse signal waveform of the subject.

5. The method of claim 4, wherein the integral function comprises $$PWF(t)_T = A\int_t^{t+T} F(ECG(u)) \cdot W(u-t) du$$

wherein $W(u-t)$ is a weight function.

6. The method of claim 4, wherein one or more of the ECG unit, memory storage, one or more hardware processors and digital display device are situated remotely from at least one other of the ECG unit, memory storage, one or more processors and digital display device.

7. A non-transitory computer-readable storage medium having stored thereon an application executable by one or more hardware processors, the execution performing:
using an ECG signal that was obtained from live tissue of a mammalian subject to generate a digital ECG signal during a period of time if a waveform of the ECG signal is not already digital;
storing a waveform of the digital ECG signal in a computer-readable memory storage;
utilizing the one or more hardware processors to constantly apply an integral function to the digital ECG signal and initiate a display signal to a digital display device to display a waveform of the integral function during the period of time, wherein the waveform of the integral function has a shape of a pulse signal waveform of the subject taken during the period of time, wherein the integral function comprises:

$$PWF(t)_T = A\int_t^{t+T} F(ECG(u)) du$$

wherein $PWF(t)_T$ is the pulse signal waveform from the ECG signal and wherein $ECG(u)$ represents the digital ECG signal over a specific time period using a specific time resolution defined by a number of sampling points per unit time, where F is a pre-processing operator on ECG to reduce or eliminate noise before integration or to smooth or sharpen the digital ECG signal before integration, wherein T is determined from the $ECG(u)$ time resolution and from a pulse or ECG peak rate in which T satisfies the Nyquist sampling theory, wherein t, u are each time variables and wherein A is a positive constant; and
constantly storing on the memory storage the waveform of the integral function having the shape of the pulse signal waveform, initiating a display signal to a digital display device to constantly display the waveform of the integral function having the shape of the pulse signal waveform of the subject.

8. The non-transitory computer-readable storage medium of claim 7, wherein the $$PWF(t)_T = A\int_t^{t+T} F(ECG(u)) \cdot W(u-t) du$$

integral function comprises
wherein $W(u-t)$ is a weight function.

* * * * *